(12) United States Patent
Ishizawa et al.

(10) Patent No.: US 9,440,235 B2
(45) Date of Patent: Sep. 13, 2016

(54) GENETIC TESTING METHOD AND TESTING APPARATUS

(75) Inventors: Masato Ishizawa, Hitachinaka (JP); Yoshiyuki Shoji, Mito (JP); Minoru Sano, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/883,612

(22) PCT Filed: Nov. 4, 2011

(86) PCT No.: PCT/JP2011/075441
§ 371 (c)(1),
(2), (4) Date: May 6, 2013

(87) PCT Pub. No.: WO2012/063736
PCT Pub. Date: May 18, 2012

(65) Prior Publication Data
US 2013/0224753 A1    Aug. 29, 2013

(30) Foreign Application Priority Data

Nov. 10, 2010   (JP) ................................. 2010-251576

(51) Int. Cl.
| | |
|---|---|
| *B01L 7/00* | (2006.01) |
| *C12Q 1/68* | (2006.01) |
| *G01N 35/00* | (2006.01) |

(52) U.S. Cl.
CPC ........... *B01L 7/52* (2013.01); *G01N 35/00623* (2013.01); *C12Q 1/686* (2013.01); *G01N 2035/009* (2013.01); *G01N 2035/00346* (2013.01); *G01N 2035/00366* (2013.01)

(58) Field of Classification Search
CPC .. C12Q 1/6844; G01N 35/00623; B01L 7/52
See application file for complete search history.

(56) References Cited

U.S. PATENT DOCUMENTS

| | | | |
|---|---|---|---|
| 5,475,610 A | 12/1995 | Atwood et al. | |
| 7,081,226 B1 * | 7/2006 | Wittwer et al. | 422/68.1 |
| 2006/0240462 A1 * | 10/2006 | Todd et al. | 435/6 |
| 2008/0212643 A1 * | 9/2008 | McGahhey et al. | 374/152 |
| 2009/0258412 A1 | 10/2009 | Moriwaki et al. | |
| 2009/0258413 A1 | 10/2009 | Moriwaki et al. | |
| 2009/0325234 A1 | 12/2009 | Gregg et al. | |
| 2011/0104703 A1 | 5/2011 | Maeda et al. | |

FOREIGN PATENT DOCUMENTS

| | | |
|---|---|---|
| GB | 2333250 A | 7/1999 |
| JP | 6-233670 A | 8/1994 |
| JP | 09-224644 A | 2/1997 |
| JP | 2006-115742 A | 5/2006 |
| JP | 2008-185389 A | 8/2008 |
| JP | 2009-022202 A | 2/2009 |
| JP | 2009-254258 A | 11/2009 |
| JP | 2009-254259 A | 11/2009 |
| JP | 2009-254260 A | 11/2009 |
| WO | 2009/157353 A1 | 12/2009 |

OTHER PUBLICATIONS

European Search Report received in European Application No. 11840150 dated Apr. 2, 2014.

* cited by examiner

*Primary Examiner* — David Thomas
(74) *Attorney, Agent, or Firm* — Mattingly & Malur, PC

(57) ABSTRACT

A genetic testing method and an apparatus therefor are provided, in which temperatures of a plurality of reaction tubes are independently controlled using a thermostat, a temperature detecting device, and a heating and cooling device provided on each of the reaction tubes, the reaction tubes each accommodate an amplification liquid and a component necessary for amplification, temperature is controlled at individual positions to hold the reaction tubes and at a predetermined temperature set at the individual positions according to an analysis and testing protocol predetermined at individual positions of the reaction tubes, a controlled temperature value is monitored in a reaction tube unit and a corrected value of controlled temperature is computed and stored on a reaction tube unit, a temperature of the reaction tube is controlled based on the computed value, and light emission of the amplification liquid accommodated in the reaction tube is measured.

5 Claims, 3 Drawing Sheets

GENETIC TESTING METHOD AND TESTING APPARATUS

TECHNICAL FIELD

The present invention relates to an analysis method and an apparatus for the same that qualitatively or quantitatively analyze a target nucleic acid included in a biological sample such as blood or urine, and the method and the apparatus are targeted for techniques that need temperature changes in course of amplification and detection in a reaction solution and techniques that do not need temperature changes in course of amplification and detection in a reaction solution.

BACKGROUND ART

Conventionally, for the amplification and quantification of nucleic acids included in a sample derived from a living body, nucleic acid amplification techniques such as polymerase chain reaction (in the following, PCR), which is a technique that needs temperature changes in course of amplification and detection in a reaction solution, and a loop-mediated isothermal amplification method (in the following, a LAMP method), which is a technique that does not need temperature changes in course of amplification and detection in a reaction solution. In PCR, it is necessary to periodically change sample temperatures generally in two or three types of temperature ranges for nucleic acid amplification. For example, in a typical PCR method, a sample is heated at a temperature of 94° C. to separate a double strand into single strands, annealed at a temperature of 60° C., and kept at a temperature of 60 to 72° C. for a few minutes. The PCR process is repeated for n times to amplify a target nucleic acid of an object. On the other hand, in the LAMP method, reactions proceed at a constant temperature, at a temperature of 60 to 65° C. In the LAMP method, amplification is performed at a certain constant temperature range as described above. Since it is important to accurately control the temperatures of a plurality of reaction tubes at a predetermined temperature, the present invention is also applicable to the LAMP method. Moreover, the amplification temperature is sometimes different depending on samples.

In order to implement this periodical temperature control method in PCR, in Patent Literature 1 described below, an apparatus is disclosed in which the apparatus includes regions, in which the temperature is kept at different set temperatures, and a disc-like sample holder and the temperature of a sample is periodically changed by rotating a disc.

However, in PCR, temperature and time necessary for an annealing reaction to bind primers having a complementary sequence to a base sequence to be detected are different depending on sequences. Moreover, temperature and time necessary in an extension reaction are different depending on enzymes to be added. Thus, in order to simultaneously process base sequences to be detected, that is, a plurality of reaction solutions in different protocols, it is necessary to provide a nucleic acid amplifier, in which temperature and time defined by a protocol is set, by the number of protocols to be simultaneously processed.

Furthermore, such a technique is known in which a plate is included to hold a plurality of samples and the temperature of the entire region of the plate is uniformly controlled. However, in PCR, a single temperature cycle is formed of a denaturation reaction, annealing reaction, and extension reaction, a certain number of cycles is repeated, and then analysis is ended. In the technique in which the entire region of the plate is uniformly controlled at a constant temperature, a new sample cannot be started for analysis after starting analysis of a sample, even though the new sample is in the same protocol, and it is necessary to wait for the end of analysis. Thus, the technique has a problem in that analysis time until the analyzed result of a new sample is obtained is prolonged.

CITATION LIST

Patent Literature

Patent Literature 1: Japanese Patent Application Laid-Open Publication No. 2008-185389
Patent Literature 2: Japanese Patent Application Laid-Open Publication No. H09-224644
Patent Literature 3: Japanese Patent Application Laid-Open Publication No. 2006-115742

SUMMARY OF INVENTION

Technical Problem

It is an object of the present invention to provide a highly reliable method and apparatus for detecting genes, in which a temperature controller is individually provided on temperature adjusting blocks in which a reaction tube is held in order to enable simultaneous processing of a plurality of types of reaction solutions in different protocols and enable starting processing of a different reaction solution even during analysis. In the method and the apparatus, in the provision of the temperature controllers, individual differences between a plurality of the temperature controllers due to factors possibly caused in industrial products are eliminated, and an abnormal operation of the temperature control mechanism of the reaction tube for amplification of a target nucleic acid can be easily recognized.

Solution to Problem

According to an aspect of the present invention, a genetic testing method and a testing apparatus can be provided, in which a genetic testing apparatus includes: a heating and cooling unit that houses a plurality of reaction tubes and controls temperature at individual positions to hold the reaction tubes, the reaction tubes each accommodating a target nucleic acid to be amplified and a component necessary for amplification; a temperature monitoring unit that monitors a controlled temperature value of the reaction tube; and a light emission detecting unit that measures light emission of a reaction solution accommodated in the reaction tube. The genetic testing apparatus includes a function in which a controlled temperature value is monitored in a unit of the reaction tube and a controlled temperature value is corrected in a unit of the reaction tube.

Advantageous Effects of Invention

According to an aspect of the present invention, the temperature controller is individually provided on the reaction tubes in order to enable simultaneous processing of a plurality of types of reaction solutions in different protocols and enable starting processing of a different reaction solution even during analysis. The provision of the temperature controllers causes dimension errors between the temperature adjusting blocks in which the tube is held and individual differences between electric heating devices and between temperature detecting devices, and the block and the devices configure the temperature controller. Factors possibly caused in industrial products such as deterioration over time in the devices cause individual differences between the temperature controllers. For the dimension errors, the individual differences between the devices, and the individual differences between the temperature controllers, a difference between a target temperature and an actual temperature caused in the individual reaction tubes controlled by a plurality of the temperature control mechanisms can be controlled within a certain range. Thus, even though a temperature cycle is performed by any temperature control mechanism of a plurality of the temperature control mechanisms, it is possible to highly accurately control temperature while maintaining equivalent performances between the positions to hold the reaction tubes. Moreover, it is possible to provide a highly reliable apparatus that can easily recognize an abnormal operation in the apparatus.

DESCRIPTION OF EMBODIMENTS

Figure 1:
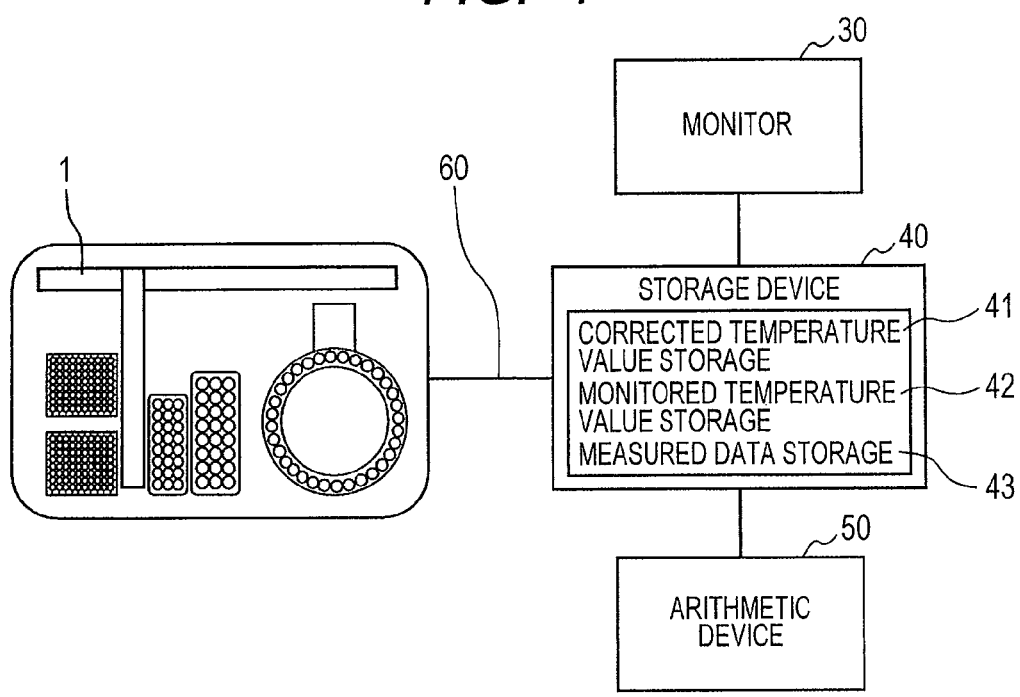
FIG. 1 is a schematic diagram of the overall structure of a genetic testing apparatus according to an example of the present invention.

The present invention relates to a genetic testing apparatus including: a plurality of reaction tubes each provided with a temperature variable temperature control mechanism for nucleic acid amplification by PCR reaction; a unit that heats and cools the reaction tube and a unit that detects the temperature of the reaction tube, the units individually provided on holder portions for the reaction tubes; a storage unit that stores a corrected temperature value, a monitored temperature, and measured data; a unit that compares stored data with a measured value of the reaction tube and computes a corrected temperature value; a unit that corrects the temperature of the reaction tube based on the corrected value; and a detector that applies pumping light to a reaction solution in the reaction tube after amplification and detects light emission such as fluorescence.

The temperature of the temperature control mechanism for each reaction tube is corrected, so that temperature can be highly accurately controlled. The transition of stored corrected temperature values is monitored, so that it is also useful to monitor an abnormal state or useful for the purpose of prevention and integrity. Moreover, a highly reliable apparatus can be provided in which a monitored controlled temperature value during execution of a nucleic acid detection protocol or measured data of detected fluorescence is displayed on the manipulation screen of the apparatus and an apparatus operator can easily recognize the presence or absence of an abnormality of temperature control in measured data.

The present invention is to provide a highly reliable apparatus that can reduce individual differences between a plurality of temperature adjusting devices due to factors possibly caused in industrial products because a temperature controller is individually provided on the reaction tubes and can easily recognize an abnormal operation in the apparatus. The apparatus includes a unit that stores a corrected controlled temperature value, temperature control data, and measured fluorescence data of a plurality of tube holder portions, and monitors and displays stored values using an arithmetic device that controls the overall apparatus.

Moreover, in the present invention, a plurality of protocols with different temperature cycles can be analyzed simultaneously. Even though analysis already proceeds in the apparatus, a new sample can be analyzed. It can be said that this is a practical feature in the case where the present invention is applied not only to PCR but also to a LAMP method. In the present invention, a genetic testing method and a testing apparatus are provided in which a measured result can be easily traced by displaying temperature control data during execution of an analysis protocol and an analyzed result profile on a screen.

Furthermore, the present invention is performed, so that it is possible to highly accurately control temperature while maintaining equivalent performances between the positions to hold the reaction tubes even though a temperature cycle is performed by any temperature control mechanism of a plurality of the temperature control mechanisms.

In addition, it is possible to provide a highly reliable apparatus that can easily recognize or predict an abnormal operation in the apparatus.

In the present invention, in the case where a PCR method is used to detect genes, a reaction tube accommodates a buffer solution, for example, to provide an optimum temperature environment in which a target nucleic acid to be amplified, primers, a target nucleic acid polymerase, deoxynucleotide triphosphate (dNTP) that is a material (a substrate) for target nucleic acid rigidity, and an enzyme work. Also in a LAMP method, a reaction tube accommodates necessary components for amplification. Since the LAMP method itself is a well-known method, the detailed description is omitted.

In the following, an embodiment of the present invention will be described.

(1) A genetic testing method includes: independently controlling temperatures of a plurality of reaction tubes using a thermostat, a temperature detecting device, and a heating and cooling device additionally provided on each of the reaction tubes, the reaction tubes each accommodating a target nucleic acid to be amplified and a component necessary for amplification; controlling temperature at individual positions to hold the reaction tubes and at a predetermined temperature set at the individual positions according to an analysis and testing protocol predetermined at individual positions of the reaction tubes; outputting a controlled temperature value of the reaction tube to a monitor; monitoring a controlled temperature value in a unit of the reaction tube and computing a corrected value of a controlled temperature value in a unit of the reaction tube; controlling temperatures of the reaction tubes; and measuring light emission of amplification accommodated in the reaction tube.

In a preferred embodiment of the present invention, it is necessary to independently control temperature at individual positions to hold the reaction tubes and at a predetermined temperature set at the individual positions according to an analysis and testing protocol predetermined at individual positions of the reaction tubes. Thus, the temperatures of a plurality of the reaction tubes can be individually controlled and monitored, so that correction can be independently performed in a unit of the reaction tube, and a difference between the actual temperature of the reaction tube and the target temperature can be made smaller. Moreover, correction can be performed on each temperature adjusting device, so that individual differences between a plurality of temperature controllers can be reduced.

In the present invention, the controlled temperature value is a controlled temperature range of a reaction tube determined by a genetic testing protocol, and is a predetermined temperature range including allowable errors. Moreover, the corrected temperature value is a corrected value changed due to the specification of the apparatus, components, an environment in which tests are carried out, or the like, and a corrected value is found any time by a measured value and computation. These items of data are stored on a monitored temperature value storage unit 42 and a corrected temperature value storage unit 41.

Furthermore, the temperature control unit is a unit that performs general temperature control according to the protocol. When it is determined that the temperature control unit does not correctly perform control, the controlled temperature value is corrected based on necessary data stored on the storage device.

(2) In the above-mentioned genetic testing method, an amplification reaction is performed by a PCR method.

(3) In the above-mentioned genetic testing method, an amplification reaction is performed by a LAMP method.

(4) In the above-mentioned genetic testing method, when a controlled temperature value of a specific reaction tube exceeds a normal range of stored corrected temperature values in course of a testing and detecting step, controlling a temperature of the reaction tube is stopped and remaining reaction tubes that converge on the normal range are used to continue analysis or testing. Here, analysis is preparation or pre-processing for genetic testing, and an analyzing step includes checking the temperature of a reaction device.

(5) In the above-mentioned genetic testing method, when a differential value between a value corrected at a present time and a value corrected at a previous time of corrected temperature values stored on a corrected temperature value storage unit exceeds a predetermined normal range, alarm is outputted.

(6) In the genetic testing method, a monitored value of controlled temperature stored on a corrected temperature value storage unit and a value of measured data of a light emission detecting unit stored on a measured data storage unit are displayed on a screen of the apparatus simultaneously, and compared with each other in a time series.

(7) A genetic testing apparatus includes: a plurality of reaction tubes each accommodating a target nucleic acid to be amplified and a component necessary for the target nucleic acid; a thermostat additionally provided on each of the plurality of reaction tubes; a temperature detecting device and a heating and cooling device additionally provided on each of the plurality of reaction tubes; a temperature control unit that controls temperature at individual positions to hold the reaction tubes and at a predetermined temperature set at the individual positions; a temperature monitoring unit that monitors a controlled temperature value of the reaction tube; a light emission detecting unit that measures light emission of a reaction solution accommodated in the reaction tube; a monitoring unit for a controlled temperature value in a unit of the reaction tube; an arithmetic unit that computes a corrected value of a controlled temperature value in a unit of the reaction tube; and a correcting unit that controls a temperature of the reaction tube.

(8) In the above-mentioned genetic testing apparatus, the correcting unit is enabled to perform a correct operation at a given execution timing.

(9) In the above-mentioned genetic testing apparatus, a temperature value of the reaction tube is enabled to be monitored at a given execution timing.

(10) In any one of the above-mentioned genetic testing apparatuses, a function is included in which when a controlled temperature value of a specific reaction tube exceeds a normal range in course of an analyzing or detecting step, a function of a temperature control unit of the reaction tube is stopped and remaining reaction tubes that converge on the normal range are used to continue analysis.

(11) In any one of the above-mentioned genetic testing apparatuses, a function is included in which when a controlled temperature value of a specific reaction tube exceeds a normal range in a preparation operation before starting analysis, a function of a temperature control unit of the reaction tube is stopped and other remaining reaction tubes that converge on the normal range are used to continue analysis.

(12) In any one of the above-mentioned genetic testing apparatuses, a function is included in which when a controlled temperature value of a specific reaction tube exceeds a normal range in a preparation operation before starting analysis, a function of a temperature control unit of the reaction tube and a function of a temperature control unit provided around the reaction tube are stopped and other remaining reaction tubes that converge on the normal range are used to continue analysis.

(13) In any one of the above-mentioned genetic testing apparatuses, a corrected temperature value storage unit is included to store temperature corrected values corrected in units of a plurality of the reaction tubes as electronic data in the apparatus.

(14) In any one of the above-mentioned genetic testing apparatuses, a function is included in which a corrected temperature value stored on the corrected temperature value storage unit is displayed on a screen of the apparatus.

(15) In any one of the above-mentioned genetic testing apparatuses, a unit is included to output alarm when a difference between a value corrected at a present time and a value corrected at a previous time of corrected temperature values stored on the corrected temperature value storage unit exceeds a normal range.

(16) In any one of the above-mentioned genetic testing apparatuses, a monitored temperature value storage unit is included to store a monitored value of controlled temperature of a reaction tube monitored by the temperature monitoring unit as electronic data in the apparatus.

(17) In any one of the above-mentioned genetic testing apparatuses, a function is included in which a monitored value of controlled temperature stored on the monitored temperature value storage unit is displayed on a screen of the apparatus.

(18) In any one of the above-mentioned genetic testing apparatuses, a unit is included to output alarm when a monitored value of controlled temperature of a reaction tube monitored by the temperature monitoring unit exceeds a normal range.

(19) In any one of the above-mentioned genetic testing apparatuses, a measured data storage unit is included to store a value of measured data of the light emission detecting unit measuring light emission of a reaction solution accommodated in a reaction tube as electronic data in the apparatus.

(20) In any one of the above-mentioned genetic testing apparatuses, a function is included in which a value of measured data of the light emission detecting unit stored on the measured data storage unit is displayed on a screen of the apparatus.

(21) In any one of the above-mentioned genetic testing apparatuses, a function is included in which a monitored value of controlled temperature stored on the monitored temperature value storage unit and a value of measured data of the light emission detecting unit stored on the measured data storage unit are enabled to be displayed on a screen of the apparatus simultaneously and enabled to be compared with each other in a time series. With the configurations, an operator can easily and quickly determine whether a temperature state is normal or abnormal in the genetic testing apparatus.

In the following, according to an example of the present invention will be described in detail with reference to the drawings.

EXAMPLE

FIG. 1 is a schematic diagram of the overall structure of a nucleic acid analyzer to which the present invention was implemented. A nucleic acid analyzer 1 is connected to a monitor 30, a storage device 40, and an arithmetic device 50 through a communication cable 60, and the monitor is operated as a manipulating unit to control the nucleic acid analyzer 1. The storage device 40 includes a corrected temperature value storage unit 41, a monitored temperature storage unit 42, and a measured data storage unit 43.

Figure 2:
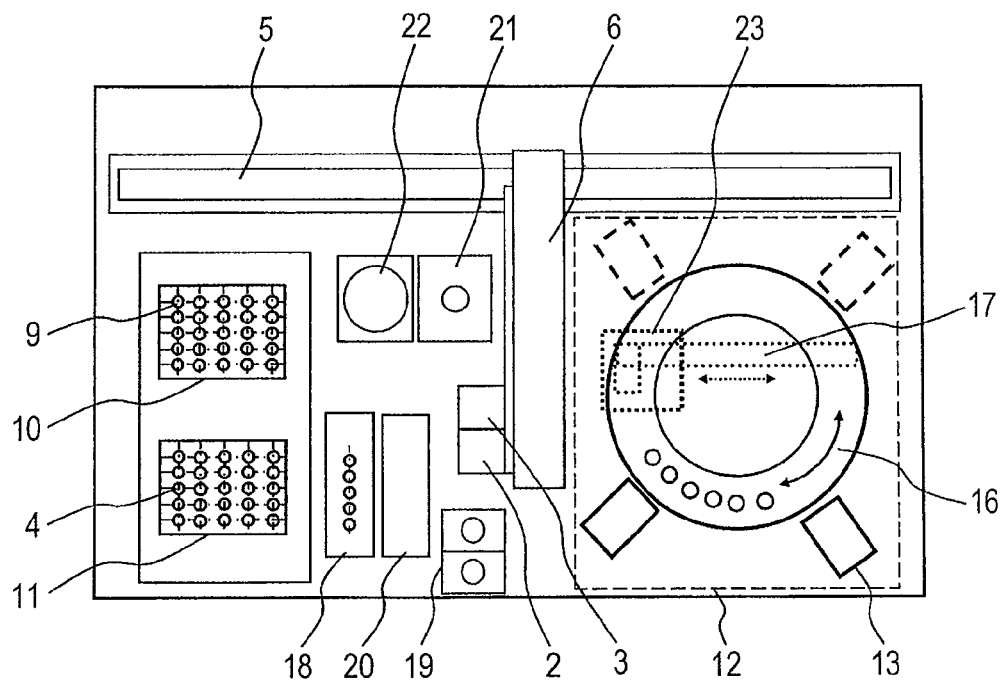
FIG. 2 is a schematic diagram of the internal configuration of the genetic testing apparatus according to an example of the present invention.

FIG. 2 is a block diagram of the inside of the nucleic acid analyzer 1. Main mechanisms and components in FIG. 2 will be described. A dispensing unit 2 sucks and discharges a liquid. A gripper unit 3 holds a reaction tube 4 one by one. The dispensing unit 2 and the gripper unit 3 are connected to a robot arm X-shaft 5 and a robot arm Y-shaft 6, and moved on a plane, and can move a reaction tube in the grip of the gripper unit 3 according to a predetermined procedure.

A dispenser chip 9 is stocked on a nozzle chip rack 10. The dispenser chip 9 is a single-use (disposable) chip in order to prevent contamination. The reaction tube 4 is a container to which a sample and a reagent are discharged, and stocked on a reaction tube rack 11.

Figure 4:
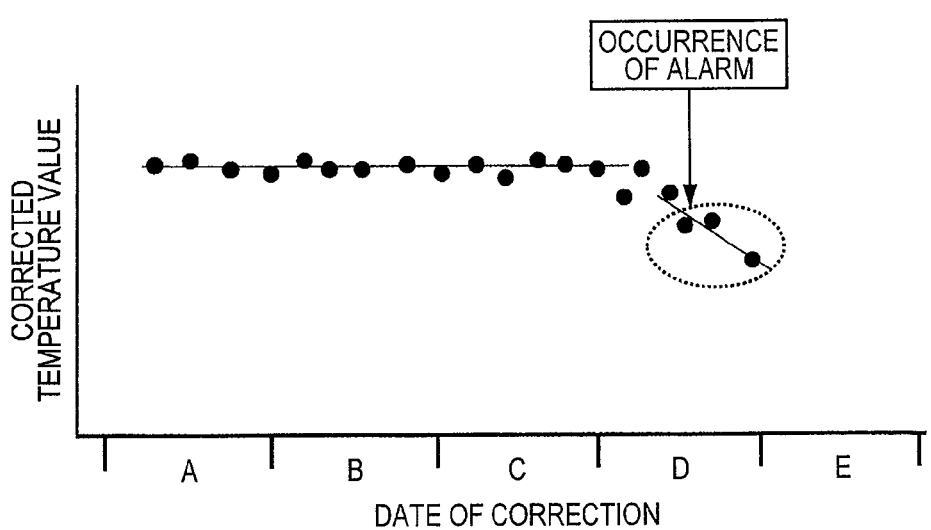
FIG. 4 is a graph of a specific example of transitions and monitoring of corrected temperature values according to an example of the present invention.

A nucleic acid amplification unit 12 according to the example of the present invention is configured of a plurality of thermostats 16, a robot arm 17 disposed above the thermostats, and a plurality of detectors disposed around the thermostats 16, and a temperature detecting device 15 shown in FIG. 4, for example. Moreover, a plurality of the reaction tubes 4 can be disposed on the plurality of thermostats 16, and the reaction tubes and the thermostats are disposed in a one-to-one relationship. Thus, such a configuration is provided for temperature control in which the reaction tubes 4 can be individually controlled and monitored.

The typical operating steps of the automatic analyzer of the nucleic acid analyzer 1 are performed by transporting the reaction tube 4 to a reaction solution adjusting position 18 using the gripper unit 3.

The dispenser chips 9 are mounted on the dispensing unit 2, and a sample and a reagent are individually sucked from a sample and reagent container 19 including the sample, and discharged into the reaction tubes 4 at the reaction solution adjusting position 18. The reagent is also discharged into the reaction tubes 4 by similar procedures. The used dispenser chips 9 are disposed of in a disposal box 20 in order to prevent contamination.

The reaction tubes 4 to which the sample and the reagent are discharged are closed with lids and hermetically sealed at a closing unit 21, stirred at a stirring unit 22, and loaded into the nucleic acid amplification unit 12 for detection at a detector 13. The reaction tubes 4 after finishing the detecting step are dispose of in the disposal box 20 using the gripper unit 3. The reaction tubes 4 are loaded into and unloaded from the nucleic acid amplification unit 12 by opening and closing a gate 23. According to the example, the temperatures of the individual thermostats are heated or cooled using an electric heating device, and the temperatures are constantly monitored using a pole temperature detecting device for control so as to perform a predetermined temperature profile, so that control and management can be performed in a unit of the reaction tube even in the case where it is necessary to manage a plurality of temperatures like PCR. Therefore, the quantification step of nucleic acids by nucleic acid amplification can be easily automated.

Figure 3:
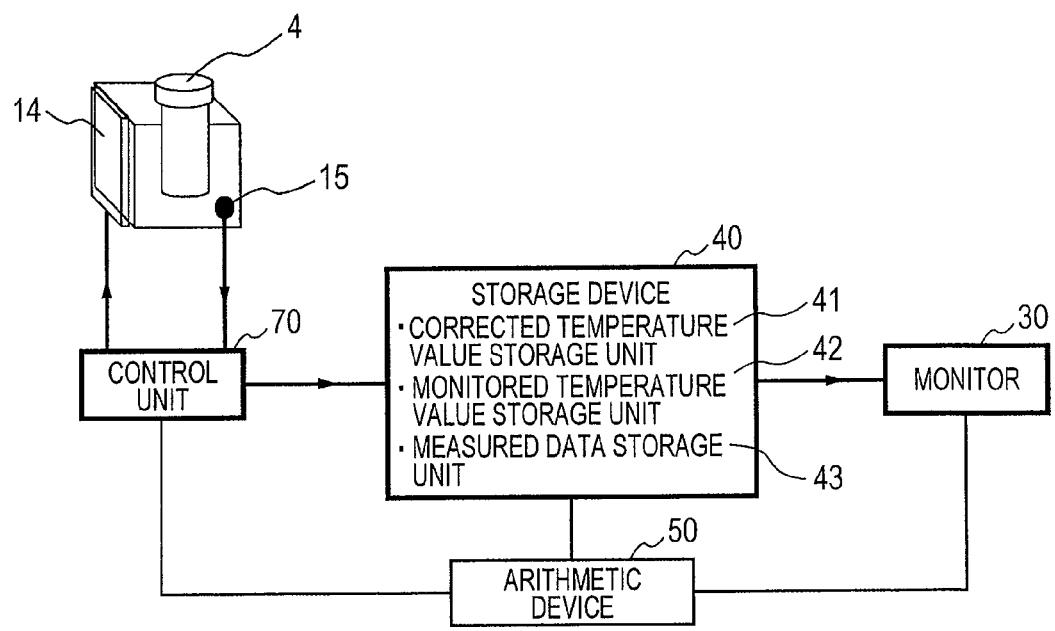
FIG. 3 is a schematic diagram of the configuration of a temperature control system according to an example of the present invention.

FIG. 3 is a schematic diagram of the configuration of a temperature control system according to the example of the present invention. Although a plurality of the reaction tubes 4 can be disposed on the thermostats 16, FIG. 3 is a conceptual diagram extracting a block diagram of a single reaction tube 4 and a control system belonging to the reaction tube 4. The controlled temperature value of a liquid accommodated in the reaction tube 4 is instructed from the computer 50, and the control system controls the temperature to increase or decrease for reaching a target temperature using an electric heating device 14. The actual temperature is then monitored using the temperature detecting device 15, and controlled to reach a target temperature.

Moreover, it is obvious that in these temperature control systems, individual differences occur between the temperature control configurations or individual differences occur between semiconductor devices such as the electric heating devices 14 and the temperature detecting devices 15. Therefore, in the present invention, such a configuration is provided in which temperature can be independently corrected for all of a plurality of the temperature control systems disposed on the reaction tubes 4, that is, disposed on the thermostats 16 on solid difference factors in the temperature control systems. Furthermore, the corrected temperature values, the monitored temperature values, and measured data detected at the detector 13 are stored as electronic data on the storage device 40, and can also be read for display on the monitor by an instruction from the computer. In addition, such a configuration is provided in which for these items of data, temperature control states can be monitored by monitoring statistical transition or the like and the alarm can be given in the case where an abnormal state is recognized.

FIG. 4 is an example when the transitions of corrected temperature values are monitored. Suppose that an operator or a service person of the apparatus can correct the temperature of temperature control configurations and can read stored corrected temperature values at a given timing. Although the corrected temperature values are varied for each correction, it can be determined that the temperature control systems are in normal states when variations converge on a specific variation range. However, as a transition shown near D in FIG. 4, in the case where it can be confirmed that a transition is clearly different from known stored values beyond a predetermined variation range, the apparatus recognizes an abnormal state and gives the alarm. However, in the case where it is confirmed that only a specific temperature control system is abnormal and the other temperature control systems are determined to be normal, preferably, such a monitoring configuration is provided in which only the temperature control system confirmed to be abnormal is stopped to operate and normal temperature control systems can continuously carry out testing operations.

Figure 5A:
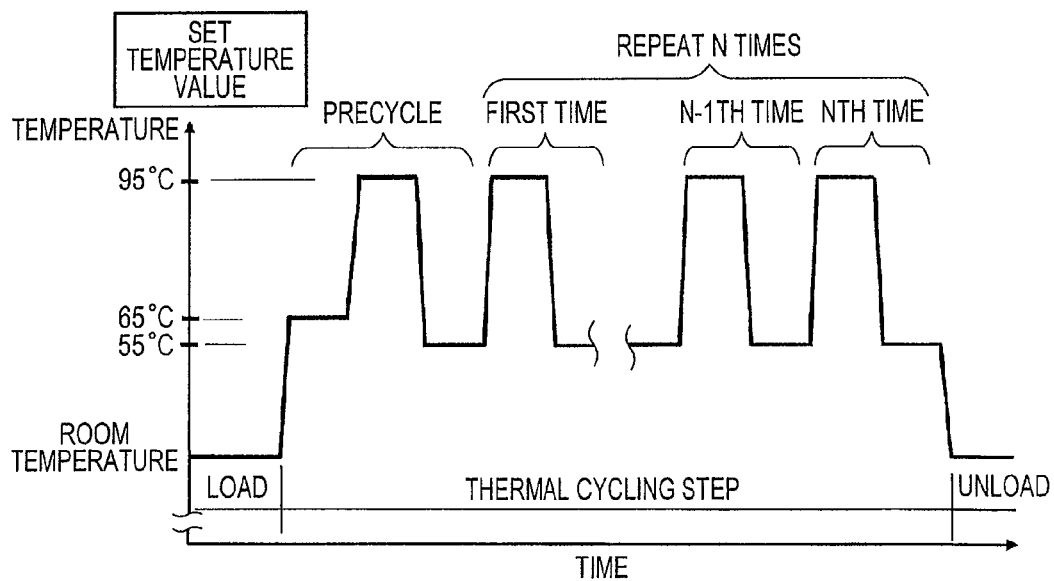
FIG. 5A is a specific example of transitions and monitoring of a temperature profile, temperature control data, and measured fluorescence data according to an example of the present invention.
Figure 5B:
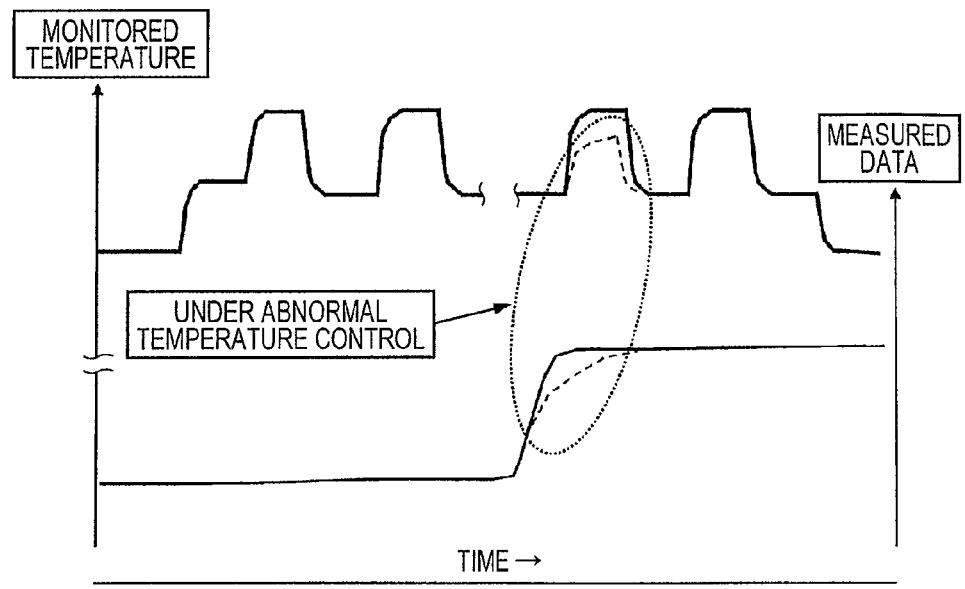
FIG. 5B is a specific example of monitoring of a temperature profile, temperature control data, and measured fluorescence data according to an example of the present invention.

FIG. 5A is a specific example of the temporal transition of increases and decreases in target temperatures in an analysis protocol, showing a target temperature profile that the temperature profile also includes temporal control factors. FIG. 5B is a specific example of the temporal transition of monitored temperature values and measured fluorescent data stored on the arithmetic device.

The temperature control system monitors the temperature of a reaction tube to be controlled on the temperature profile, also detects a fluorescent quantity as measured data simultaneously, and stores the temperature and the measured data. Ones shown in FIG. 5B are the monitored temperature values and the measured data described above. In the PCR method, it is known that the accuracy of the temperature of the reaction tube is a large factor to possibly cause variations in measured data. Moreover, in a conventional apparatus that is operated in units of batches and uniformly controls the temperature in the entire regain of a plate to increase and decrease temperatures, the locality of temperatures is large between portions to hold reaction tubes, and the temperatures of the portions to hold the reaction tubes cannot be monitored, so that such an avoidance scheme is taken in which a reaction tube is held on another portion for measurement again in the case where an abnormality arises in measured data, and such an operation is actually performed that an operator is heavily burdened.

In the present invention, such a configuration was provided in order to improve these workflows in which a monitored temperature value and measured data are displayed simultaneously on the screen of the apparatus. As shown in FIG. 5B, a monitored temperature value and measured data can be confirmed simultaneously, so that also in the case where temperature is controlled abnormally in a specific control cycle to affect the accuracy of measured data as denoted as under abnormal temperature control, in the present invention, the abnormal state can be easily recognized, and a function to give the alarm can be easily implemented in the case where a monitoring range is exceeded by specifying a specific monitoring range.

As easily apparent from the descriptions, the present invention is implemented, so that a genetic testing apparatus of high operability and high reliability can be provided, in which temperature can be controlled and monitored in a unit of a reaction tube, the alarm can be given in a unit of a reaction tube, and an abnormal state can be recognized also on the screen of the apparatus.

INDUSTRIAL APPLICABILITY

The present invention is effective as a temperature control technique for amplification and detection of genes using a PCR method or a LAMP method.

REFERENCE SIGNS LIST

1 Nucleic acid analyzer
4 Reaction tube
9 Dispenser chip
13 Detector
14 Electric heating device
15 Temperature detecting device
16 Thermostat
17 Gripper arm
20 Disposal box
23 Gate

The invention claimed is:

1. A genetic testing method comprising:
hermetically sealing and stirring a plurality of reaction tubes, each accommodating an amplification liquid including a target nucleic acid to be amplified and a component necessary for amplification;
independently controlling temperatures of each of the reaction tubes using a plurality of thermostats, a plurality of temperature detecting devices, and a plurality of heating and cooling devices independently provided for the reaction tubes to hold each of the reaction tubes at a predetermined temperature individually set for each of the respective reaction tubes according to an analysis and testing protocol predetermined for each of the respective reaction tubes;
monitoring and storing the independently controlled temperatures of each of the reaction tubes;
computing and storing corrected values of the independently controlled temperatures for each of the reaction tubes;
measuring and storing light emission of the amplification liquid accommodated in each of the reaction tubes while independently controlling the temperatures of each of the reaction tubes based on the respective corrected values;
when the corrected values of the independently controlled temperature of one of the reaction tubes exceeds a predetermined range during measurement of light emission, stopping the independent temperature control of the one of the reaction tubes while the remaining reaction tubes respectively continue the independent controlling of the temperatures and the measuring of light emission; and
simultaneously displaying the monitored values of the controlled temperatures and the measured light emission in time series on a display screen in relation to each other including the monitored value of the controlled temperature and the measurement of light emission of the amplification liquid accommodated in the one of the reaction tubes as a display of an abnormal temperature control state.

2. The genetic testing method according to claim 1, wherein an amplification reaction is performed by a PCR method.

3. The genetic testing method according to claim 1, wherein an amplification reaction is performed by a LAMP method.

4. The genetic testing method according to claim 1, further comprising:

when a difference between one of the corrected values at a first time and another of the corrected values at a second, earlier time for one of the reaction tubes exceeds a predetermined range, outputting an alarm.

5. The genetic testing method according to claim 1, further comprising:

after finishing the measurement of light emission of the amplification liquid accommodated in another one of the reaction tubes, disposing of the other one of the reaction tubes in a disposal box.

* * * * *